United States Patent
Roundhill et al.

(10) Patent No.: US 11,055,899 B2
(45) Date of Patent: Jul. 6, 2021

(54) SYSTEMS AND METHODS FOR GENERATING B-MODE IMAGES FROM 3D ULTRASOUND DATA

(71) Applicant: KONINKLIJKE PHILIPS N.V., Eindhoven (NL)

(72) Inventors: David Nigel Roundhill, Woodinville, WA (US); Benoit Jean-Dominique Bertrand Maurice Mory, Mercer Island, WA (US); Emmanuel Mocé Serge Attia-Gani, Paris (FR); Jean-Michel Rouet, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 209 days.

(21) Appl. No.: 16/308,628

(22) PCT Filed: Jun. 12, 2017

(86) PCT No.: PCT/EP2017/064223
§ 371 (c)(1),
(2) Date: Dec. 10, 2018

(87) PCT Pub. No.: WO2017/212063
PCT Pub. Date: Dec. 14, 2017

(65) Prior Publication Data
US 2019/0272667 A1    Sep. 5, 2019

Related U.S. Application Data

(60) Provisional application No. 62/418,319, filed on Nov. 7, 2016, provisional application No. 62/348,411, filed on Jun. 10, 2016.

(51) Int. Cl.
G06K 9/00    (2006.01)
G06T 15/08    (2011.01)
(Continued)

(52) U.S. Cl.
CPC .......... *G06T 15/08* (2013.01); *A61B 8/5246* (2013.01); *G06T 19/00* (2013.01); *A61B 8/5207* (2013.01);
(Continued)

(58) Field of Classification Search
CPC ..... G06T 15/08; G06T 19/00; G06T 2200/24; G06T 2210/41; G06T 2219/008; A61B 8/5246; A61B 8/5207; G16H 30/40
(Continued)

(56) References Cited

U.S. PATENT DOCUMENTS 5,787,889 A * 8/1998 Edwards ................. A61B 8/14
                                                              600/443
6,480,732 B1 * 11/2002 Tanaka ................. A61B 8/5238
                                                              128/922
(Continued)

FOREIGN PATENT DOCUMENTS

DE    10210466 A1    10/2003
JP    5936850 A    6/2013

OTHER PUBLICATIONS

Yang, et al., "Practical Guide for Three-Dimensional Transthoracic Echocardiography Using a Fully Sampled Matrix Array Transducer", Review Article, Journal of American Society of Echocardiography, vol. 21, No. 9, Sep. 1, 2008, pp. 979-989. (Year: 2008).*

(Continued)

*Primary Examiner* — Van D Huynh

(57) ABSTRACT

The present disclosure describes a medical imaging and visualization system that provides a user interface enabling a user to visualize a volume rendering of a three dimensional (3D) data set and to manipulate the volume rendering to dynamically select a MPR plane of the 3D data set for generating a B-mode image at the dynamically selected (Continued)

MPR plane. In some examples, the 3D data set is rendered as a 2D projection of the volume and a user control enables the user to dynamically move the location of the MPR plane while the display updates the rendering of the volume to indicate the current location of the MPR plane and/or corresponding B-mode image.

15 Claims, 13 Drawing Sheets

(51) Int. Cl.
    *A61B 8/08*         (2006.01)
    *G06T 19/00*      (2011.01)
    *G16H 30/40*     (2018.01)

(52) U.S. Cl.
    CPC ...... *G06T 2200/24* (2013.01); *G06T 2210/41* (2013.01); *G06T 2219/008* (2013.01); *G16H 30/40* (2018.01)

(58) Field of Classification Search
    USPC .......................................................... 382/128
    See application file for complete search history.

(56) References Cited

U.S. PATENT DOCUMENTS

| | | |
|---|---|---|
| 7,889,194 B2 | 2/2011 | Engel et al. |
| 2008/0177182 A1* | 7/2008 | Takimoto ............... A61B 8/483 600/441 |
| 2010/0185094 A1* | 7/2010 | Hamada ................. A61B 6/466 600/443 |
| 2011/0144499 A1* | 6/2011 | Yoo ........................... A61B 8/14 600/443 |
| 2013/0012820 A1* | 1/2013 | Brown ................... A61B 8/466 600/443 |
| 2015/0065877 A1* | 3/2015 | Orderud ............... A61B 8/5253 600/438 |
| 2015/0294497 A1* | 10/2015 | Ng ......................... A61B 8/466 382/128 |

OTHER PUBLICATIONS

Shen, et al., "GPU-Based Realtime Hand Gesture Interaction and Rendering for Volume Datasets using Leap Motion", 2014 International Conference on Cyberworlds, IEEE, Oct. 6, 2014, pp. 85-92. (Year: 2012).*

Yang, et al., "Practical Guide for Three-Dimensional Transthoracic Echocardiography Using a Fully Sampled Matrix Array Transducer", Review Article, Journal of American Society of Echocardiography, vol. 21, No. 9, Sep. 1, 2008, pp. 979-989.

Lang, et al., "EAE/ASE Recommendations for Image Acquisition and Display Using Three-Dimensional Echocardiography", European Heart Journal, Cardiovascular Imaging, vol. 13, No. 1, Jan. 1, 2012, pp. 1-46.

Shen, et al., "GPU-Based Realtime Hand Gesture Interaction and Rendering for Volume Datasets using Leap Motion", 2014 International Conference on Cyberworlds, IEEE, Oct. 6, 2014, pp. 85-92.

* cited by examiner

SYSTEMS AND METHODS FOR GENERATING B-MODE IMAGES FROM 3D ULTRASOUND DATA

This application is the U.S. National Phase application under 35 U.S.C. § 371 of International Application No. PCT/EP2017/064223, filed on Jun. 12, 2017, which claims the benefit of both Provisional Application Ser. No. 62/418,319, filed Nov. 7, 2016 and Provisional Application Ser. No. 62/348,411, filed Jun. 10, 2016. These applications are hereby incorporated by reference herein.

BACKGROUND

While conventional two-dimensional (2D) ultrasound remains a clinically important technique for medical imaging, advents in rendering techniques to provide images with high degree of anatomical realism are increasing the popularity of 3D ultrasound. 3D ultrasound is an imaging technique which acquires a 3D data set corresponding to an imaged volume of biological tissue. One advantage of 3D ultrasound is the ability to reconstruct a plane of any arbitrary orientation through the imaged volume during or post data acquisition. This technique is referred to a multiplanar reformatting or reconstruction. In conventional systems, a multiplanar reformatter generally produces standard orthogonal views (e.g., in the axial, sagittal or coronal planes) or an oblique plane specified by the user. Identifying the specific plane of interest with conventional systems can be cumbersome, typically requiring a skilled operator to navigate through the volume data to identify the desired plane. A more intuitive and/or interactive approach to generating 2D slices through an imaged volume may be desired.

SUMMARY

In accordance with some examples, an ultrasound imaging system may include an ultrasound probe configured to receive ultrasound echoes from a subject to image a volume of the subject. The ultrasound imaging system may further include a scan converter configured to arrange echo signals in a 3D dataset corresponding to the imaged volume, and a volume renderer configured to render a 2D projection image of the 3D data set and further configured to receive user input indicative of a location of a cut plane relative to the 3D dataset. The ultrasound imaging system may include a multiplanar reformatter (MPR) configured to generate a B-mode image of a slice through the imaged volume corresponding to the location of the cut plane. The ultrasound imaging system may also include a user interface which includes at least one output device and at least one input device. The output device may include a display configured to display 2D projection images generated by the volume renderer and/or B-mode images from the MPR. In some examples, the 2D projection images and the B-mode images are displayed side by side. In other examples, the ultrasound imaging system is configured to generate and display an overlay image of the B-mode image and the 2D projection image. In some examples, only the 2D projection image is displayed, while the B-mode images corresponding to selected cut planes are output for storage in a memory and/or for inclusion in a report.

The input device of the ultrasound imaging system may include one or more physical controls (e.g., push buttons, a keyboard, a touchpad, a trackball or other rotary controls, or a touch screen which displays graphical user interface widgets, also referred to as soft controls), which may be provided on a control panel of the ultrasound imaging system. In some examples, the ultrasound imaging system may additionally or alternatively include a touchless interface which enables the user to provide inputs without physically touching a control panel of the ultrasound imaging system. In some examples, the input device of the ultrasound imaging system is configured to receive user input for dynamically positioning a cut plane in relation to a 3D dataset that has been rendered on the display. The volume renderer may be further configured to dynamically update, responsive to the user input, the 2D projection image to visualize the location of the cut plane in relation to the 3D dataset and to communicate to the MPR the location of the cut plane for generating a corresponding MPR slice of the imaged volume.

A method in accordance with the present disclosure may include receiving a 3D dataset corresponding to an ultrasonically imaged volume of biological tissue, generating a volume rendering of the 3D dataset, displaying the volume rendering on a display, receiving user input to change a location of a cut plane relative to the 3D dataset, updating the volume rendering to display a cut-away view of the 3D dataset, wherein the cut-away view includes only a portion of the 3D dataset coincident with and located on one side of the cut plane, and automatically generating a B-mode image at a plane of the 3D dataset coincident with the cut plane.

Additionally, any of the techniques for manipulating and rendering 3D dataset and/or extracting B-mode images from the 3D dataset may be embodied in executable instructions stored on non-transitory computer-readable medium, which when executed cause a processor of a medical imaging system to be programmed to perform the processes embodied in the non-transitory computer-readable medium.

DETAILED DESCRIPTION

Figure 1A:
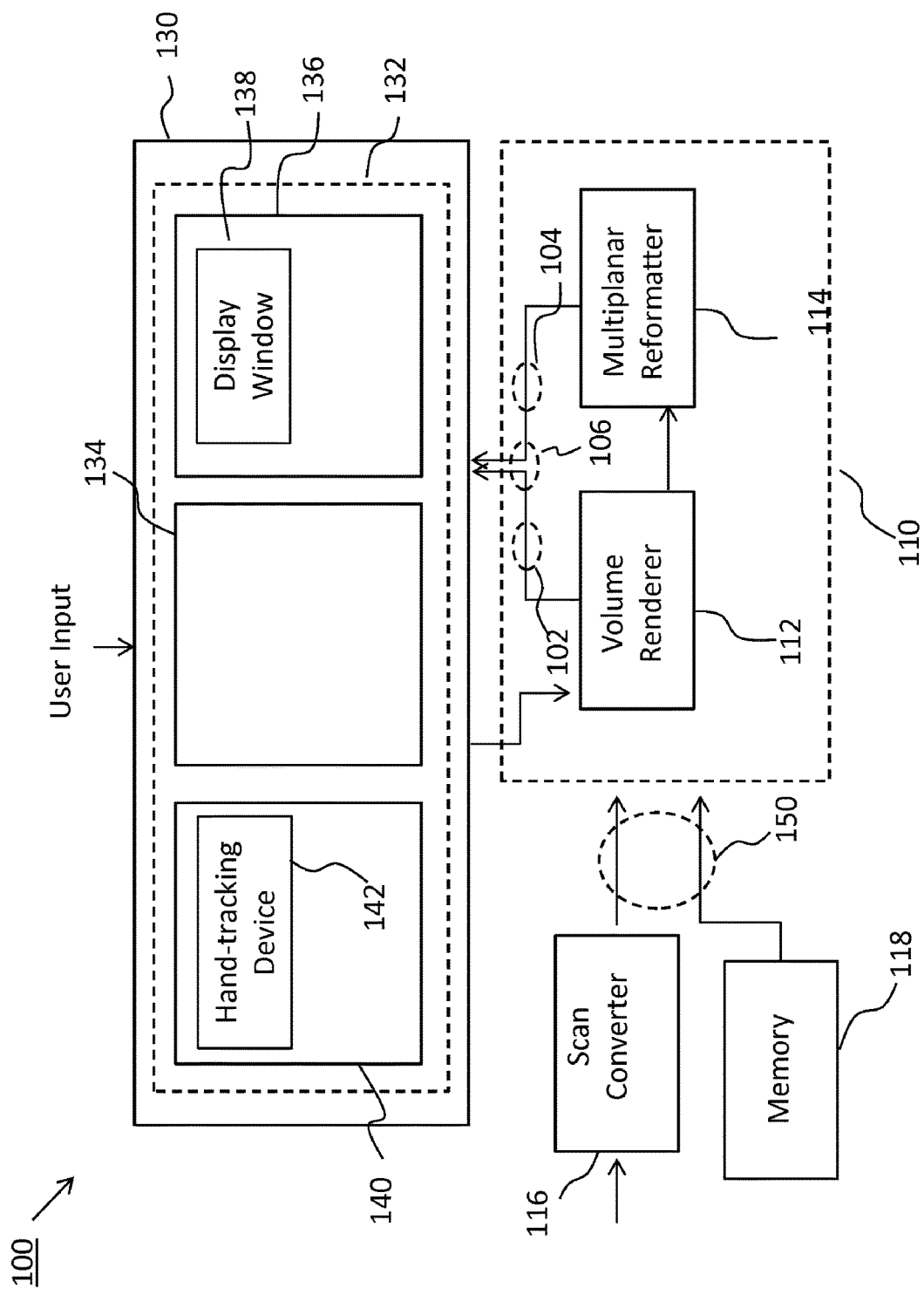
FIG. 1A is a block diagram of a system in accordance with the principles of the present disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In medical imaging, images of biological tissue may be rendered in real time or post-data set acquisition. The images may be 2D images corresponding to a single plane or slice through the imaged tissue of a subject (e.g., a B-mode ultrasound image) or they may be 2D renderings of the imaged volume (e.g., a 3D ultrasound image). 2D slices or planes are ubiquitously used in various clinical applications, such as during diagnosis, treatment, or surgical planning, to non-invasively obtain information about structures of or in an organ or tissue of the subject. Advancements in medical imaging systems now provide the ability to generate volume renderings with high degree of anatomical realism, which is increasingly enabling a clinician to view patient anatomy in a highly intuitive manner. For example, ultrasound sonography, which is the preferred modality for pre-natal monitoring, is now generally capable of providing volume renderings of an imaged fetus. However, such volume renderings have thus far been of limited or no value to the sonographer, as 2D slices through a region of interest are ultimately used to obtain clinically relevant information and measurements and are typically required for inclusion in the ultrasound report. The systems and methods described herein may enable the use of volume renderings such as to provide greater clinical value in medical imaging applications. For example, a keen understanding of orientation when viewing 2D images of slices is essential to understanding what is being seen in the image. Often, a significant time is expended during an imaging session for the operator to orient themselves and ensure that the right 2D plane is being acquired. The systems and techniques described herein may enable an operator to more efficiently and intuitively identify the appropriate 2D slice for inspection and/or inclusion in a report.

Figure 1B:
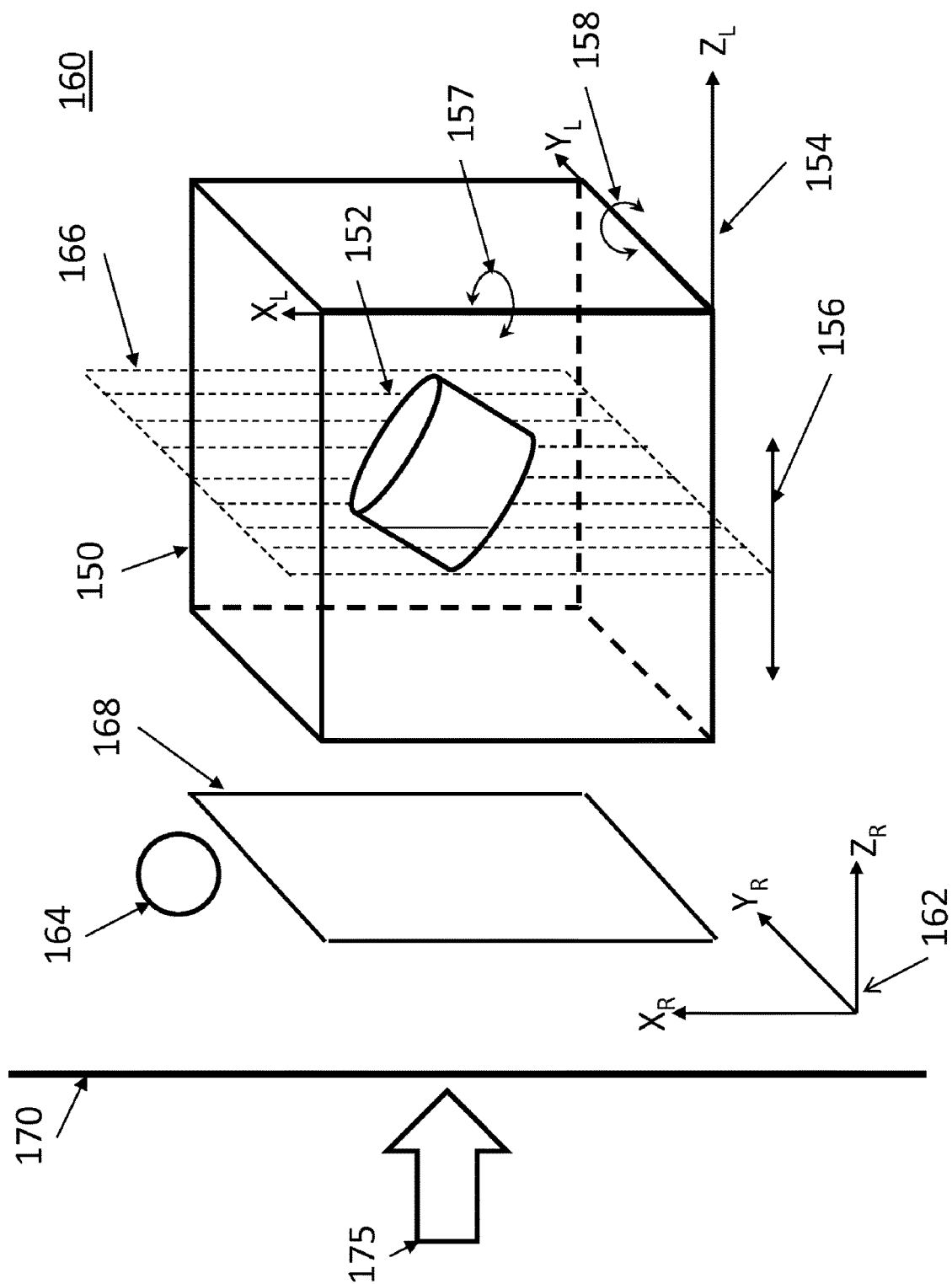
FIG. 1B is an illustration of a 3D dataset in a rendering environment in accordance with the principles of the present disclosure.

FIG. 1 shows an example system 100 which is configured to generate B-mode images from a 3D dataset in accordance with the present disclosure. The system 100 may include a volume renderer 112, a multiplanar reformatter 114, and a user interface 130, which includes a display operable to display images (e.g., B-mode images 106, volume renderings 104, and overlays 106 of the two) generated by the system 100. Images may be generated from the 3D dataset and displayed in real time (e.g., during data acquisition) or post acquisition. As is well known, a B-mode image is a gray-scale image that represents, for the given plane, the intensity of the received echoes by modulating the brightness of corresponding pixels in the image. On the other hand, a 3D volume rendering may be produced using any known volume rendering technique, for example isosurface extraction, volume ray casting, splatting, shear warping, texture-based volume rendering, maximum intensity projection, and others. For example, a 2D projection of the volume may be obtained by casting of virtual rays into the imaged volume. When rays are cast from a virtual observer's position towards a region of interest within an imaged volume, various anatomic structures may be interposed along the line of sight. A simulated light source may be used to provide depth perception and incoming light direction drives the appearance of shadows and reflections in the volume rendering. While volume renderings of 3D dataset of medical imaging data have been produced with known systems, such volume renderings have thus far been of limited use to the sonographer or a treating physician, as the clinical community almost entirely relies upon conventional 2D B-mode images for the relevant information needed to make diagnosis or plan treatment.

The principles described herein may provide a new clinically relevant application for volume rendering of 3D datasets, one of these applications being the easy and efficient identification of the relevant plane for extraction of B-mode images from the 3D dataset. In this regard, the system 100 may be configured to dynamically update the 2D projection image of an imaged volume in real time responsive to user inputs to enable a user to visualize the changing location of the cut plane in relation to the rendered volume and/or the corresponding MPR slice through the volume. The location of the cut plane is communicated to the MPR in real time (e.g., during manipulation of the volume) such that the MPR can automatically reconstruct the corresponding MPR slice from the 3D dataset without the user having to manually identify the desired plane for the MPR slice.

The volume renderer 112 may receive the 3D dataset 150 and generate a volume rendering 102 of the 3D dataset for display. In some examples, the volume renderer 112 may receive the 3D dataset from a scan converter 116 of an ultrasound imaging system, which is configured to arrange echo signals acquired with the ultrasound imaging system into the 3D dataset 150. In other examples, the 3D dataset 150 may be retrieved from a memory 118, which may be memory of an imaging system, such as the ultrasound imaging system which was used to acquire the 3D dataset, a storage device of a picture archiving and communication system (PACS), or a portable memory device. The volume renderer may be operatively associated with a user interface 130 which includes one or more user input devices (e.g., control panel, touch screen, touchless interface). The user interface may enable the user to manipulate the rendered volume within a rendering environment (e.g., a 3D virtual or rendering space).

Figure 2:
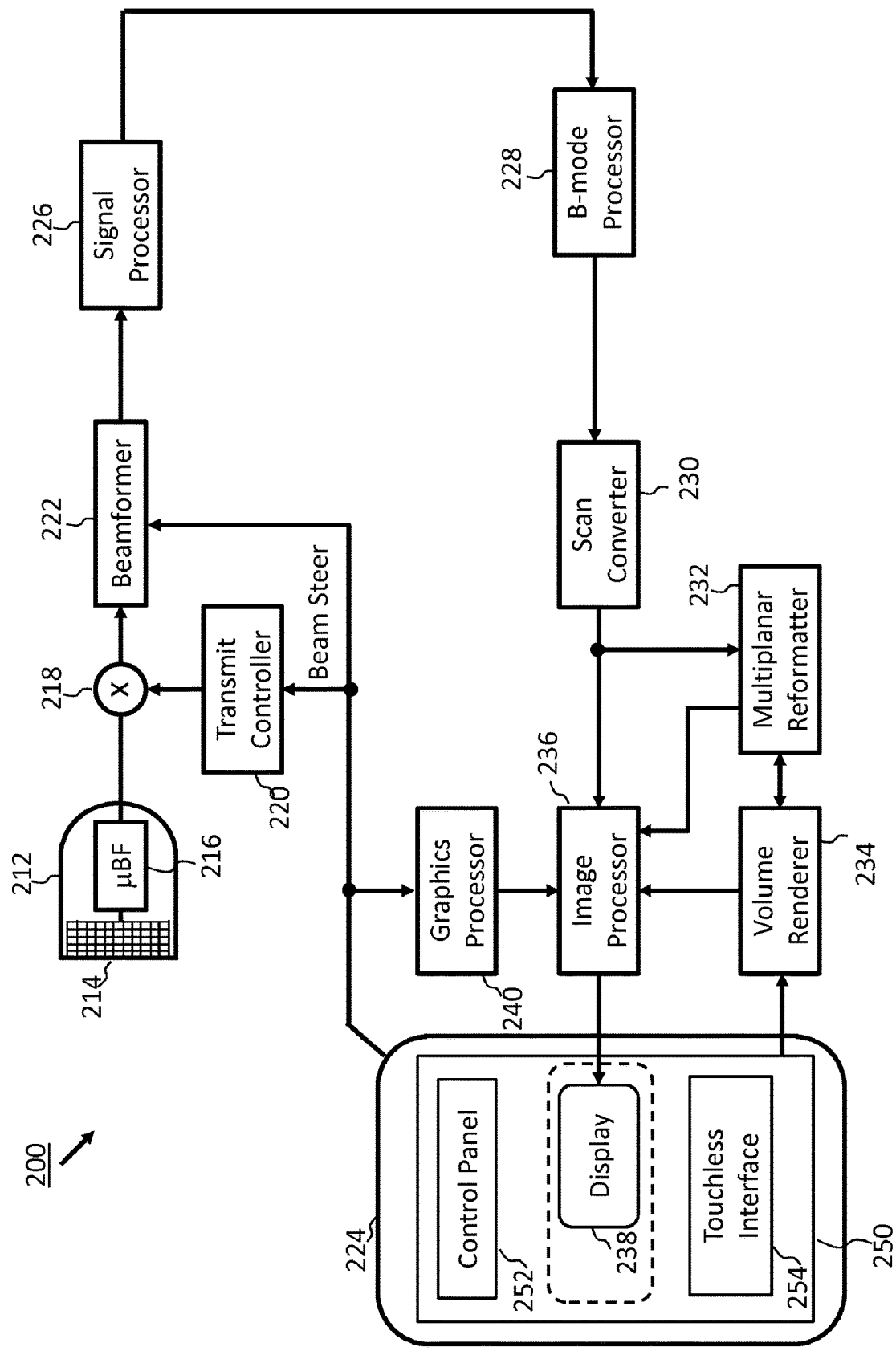
FIG. 2 is a block diagram of an ultrasound imaging system according to some embodiments of the present disclosure.

Referring now also to FIG. 2, a 3D dataset 150 is shown in a rendering environment 160, also referred to as virtual space. The 3D dataset 130 may correspond to an imaged volume of biological tissue and may include one or more regions of interest 135. The region of interest 135 may be a portion of an object (e.g., wall of blood vessel, valve of heart) or may be an entire object (e.g., tumor, fetus). For ease of illustration, the 3D dataset 130 and region of interest 135 are illustrated with simple geometric shapes however in some examples, they may be differently shaped. The 3D dataset 130 in this example is illustrated in the rendering environment along with a number of rendering constructs. A rendering coordinate frame 162 may be associated with the rendering environment 160, while the 3D dataset may be defined in relation to a local coordinate system 154, which may be the reference frame of the ultrasound probe used to acquire the dataset. Alternatively, the location of any of the rendering constructs or the point of view of the observer 175 may be defined relative to the coordinate frame of the 3D dataset. When generating a volume rendering, the relative position of the 3D dataset to a projection plane 170, which may be the X-Y plane of the rendering coordinate frame 162, and a viewpoint of a virtual observer, which is typically normal to the projection plane 170, are set, typically based on default parameters. The relative position and orientation of the 3D dataset to the projection plane 170 may be varied by the user during manipulation of the volume within the rendering environment.

The 3D data set and any other of the rendering constructs may be movable in relation to one another and within the virtual space. In some examples, the simulated light source 164, the cut plane 166, and the 3D dataset 150 may be moved (e.g., translated and/or rotated), responsive to user inputs, relative to one another and/or in relation to the coordinate frame 162 and correspondingly relative to the projection plane 170. For example, responsive to user input, the cut plane 166 may be translated normally to the projection plane, as indicated by arrow 156 and/or rotated about any of the $X_L$ and $Y_L$ axes, as shown by arrows 157 and 158, respectively, or axes parallel thereto. Translation and rotation of the cut plane 166 relative to the 3D dataset may be responsive to user inputs via conventional (e.g., physical controls) or via a touchless interface 140. In some examples, a touchless interface 140 may be operatively connected with the volume renderer 112 such that movements of an object within a tracking field of the touchless interface are translated, by the volume renderer 112, into movements of the cut plane 166.

The 3D dataset 150 may include echo intensity information for any given point (or coordinate location) within the imaged volume. For example, in a Cartesian coordinate system, the 3D dataset 150 may include voxel data that specifies the x, y, z coordinates for each voxel in the dataset along with echo intensity value at each voxel. As described, the 2D projection image 168 of the volume onto projection plane 170 may be rendered according to known techniques, for example using ray casting and splatting. When rendering a 2D image of the 3D data set including the region of interest, the location, intensity or directionality of the simulated light source 164 may determine the shading on surfaces of the volume, which may provide depth perception for a user.

The volume renderer 112 may be configured to receive user input via the user interface 130. For example, the user interface 130 may include one or more user input devices 132 comprising physical controls such as buttons, a keyboard, a trackball, a touchpad, and/or soft controls implemented using graphical user interface (GUI) elements (also referred to as widgets). The physical controls may be provided on a control panel 134 of the system, which may in some cases include or be operatively associated with a touch screen. As previously noted, in some examples, the system 200 may alternatively or additionally include a touchless interface 140. The touchless interface 140 may include a hand-tracking device 142, for example an optical tracking device, configured to track the movement of the user's hands when presented in the tracking field of the hand-tracking device 142. In some embodiments, the hand-tracking device 142 may be implemented using the Leap Motion Controller produced by Leap Motion, Inc. In some examples, the hand-tracking device 142 may be operable to track the movements of one or both of the user's hands or portions thereof and generate tracking data identifying discrete locations and changes in location of each tracked object at regularly spaced intervals of time (e.g., every microsecond, or every few microseconds), such that complex motion of a user's hand can be mapped to manipulation commands for manipulating the volume in the rendering environment. In some examples, the volume renderer may be configured to translate the movement of one of the user's hands (e.g., the left hand) to movement of the cut plane relative to the 3D dataset, and to translate the movement of the other one of the user's hands (e.g., the right hand) to movement of the 3D dataset within the rendering environment (e.g., relative to a projection plane). In some examples, the volume rendering environment may provide a plurality of cut planes which may be disposed at an angle to one another such as to enable the user to generate B-mode images at oblique (e.g., orthogonal) planes. In such instances, movements of one hand can be translated to movements of one of the cut planes, while movements of the other hand may be translated to movements of a second cut plane.

The user interface 130 may also include one or more output devices, such as a display 136. Images (e.g., volume renderings 102, B-mode images 104) generated by system 200 may be displayed the display 136, for example in a display window 138. The display 136 may be touch-sensitive, for example using capacitive touch sensing, to provide a touch screen display, which may also function as part of the input interface. In some examples, the display may be a separate, non touch-sensitive display unit.

In accordance with the examples herein, the volume renderer 112 may receive user inputs for manipulating a volume (e.g., the rendered 3D dataset 150) within the virtual space 160. In some examples, the volume renderer 112 may receive user inputs to pan (e.g., translate in a plane parallel to the projection plane 170), zoom (e.g., translate along the $Z_R$ axis) and rotate the volume relative to the coordinate frame 162. In addition, the volume renderer 112 may receive user inputs to adjust one or more rendering constructs, such as changing the location, intensity, or directionality of the simulated light source 164, or the location and orientation of a cut plane 166 in relation to dataset 150. The volume renderer 112 may communicate the location of the cut plane 166 to the multiplanar reformatter 114, which is configured to automatically generate a B-mode image 104, also referred to as MPR image or MPR slice, at a slice plane coincident with the the cut plane 166. For example, in fetal ultrasound applications, the system may be used to generate a volume rendering of a fetus. Through a volume rendering interface, the user may interactively adjust the location of the cut plane while the volume renderer updates the rendering in real-time to display a cut-away view showing only that portion of the volume coincident with and behind the cut plane (see e.g., cut-away volume rendering of an imaged fetus in FIG. 3A), also referred to as displayed portion.

Figure 3B:
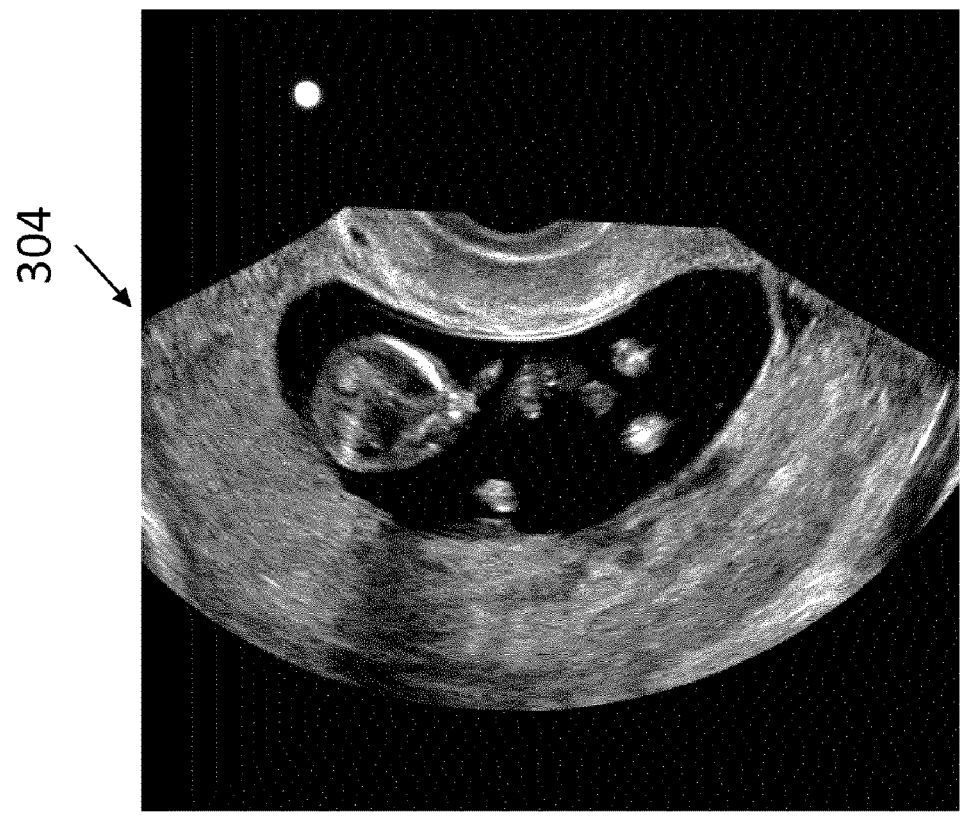
FIGS. 3A-3E are images generated in accordance with the principles of the present disclosure.
Figure 3A:
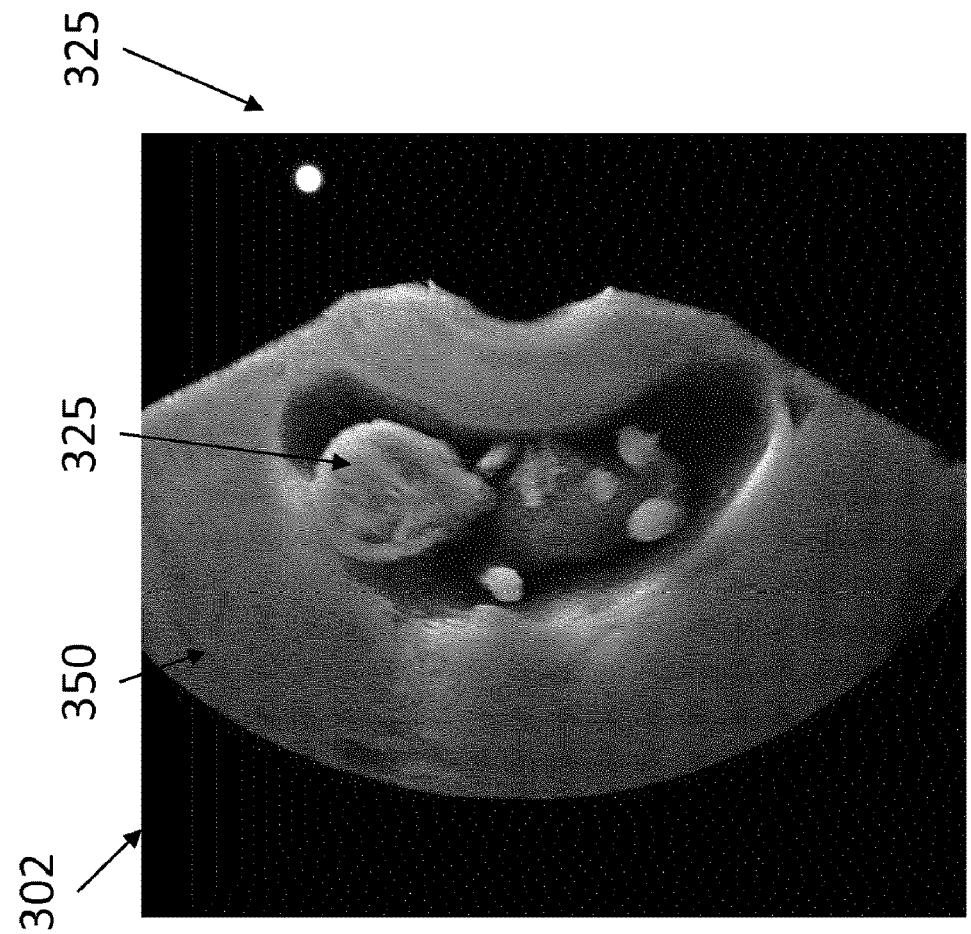

Concurrently, the multiplanar reformatter 114 generates B-mode images at the slice planes coincident with the location of each cut plane as the user interactively adjusts the location of the cut plane (see e.g. FIG. 3B showing a B-mode image corresponding to the cut-away view in FIG. 3A). Both the volume rendering and the B-mode image may be simultaneously displayed, in some cases in a side-by-side arrangement or as an overlay in the same display window (see e.g., FIG. 3C) to enable the user to interactively adjust (e.g., scroll) the location of the cut plane while visualizing the corresponding B-mode image at that slice plane. The presentation of the B-mode image concurrently with a rendering of the volume may enable the user to more easily orient and identify the relevant plane for obtaining a B-mode image of clinical relevance. The volume renderer 112 and the multiplanar reformatter 114 may be operatively associated or be part of image processing circuitry 110 of the system 100, which may additionally perform functions, such as generating overlays, annotating images, and buffering data prior to display. In this manner, by enabling the user to dynamically select the relevant slice plane while visualizing the 3D volume, system 100 may provide a more user-friendly interface which allows the user to more intuitively and efficiently extract the requisite B-mode images from a 3D imaging dataset. By dynamically selecting or moving the location of the cut plane it is meant that the interface enables the user to scroll or drag the cut plane through the volume with the rendering updating as the user drags the cut plane.

In some examples, the rendering interface may be further configured to enable the user to freeze or lock the location and orientation of the cut plane 116 relative to the volume while the volume is further manipulated (e.g., translated, rotated for example to identify another projection side for cropping) or while the simulated light is manipulated. In this regard, the volume renderer 112 may be configured to maintain the relative position between the cut plane 116 and the 3D dataset while updating the rendering responsive to user commands to move the volume. As the user manipulates the volume, the displayed portion of the 3D dataset moves relative to the observer's perspective, for example causing the face of the rendered volume coincident with the cut-plane to be arranged obliquely to the projection plane in response to the user rotating the volume.

FIG. 2 shows a block diagram of an ultrasound imaging system 200 constructed in accordance with the principles of the present disclosure. The ultrasound imaging system 200 may include one or more of the components described above with reference to FIGS. 1A-1B. Although ultrasound imaging systems are discussed in explanatory examples of embodiments of the invention, embodiments of the invention may be practiced with other medical imaging modalities. Other modalities may include, but are not limited to, magnetic resonance imaging and computed tomography. The techniques described herein may be applied to virtually any imaging modality which can be used to acquire a 3D imaging dataset.

The ultrasound imaging system 200 in FIG. 2 includes an ultrasound probe 212 which includes a transducer array 214 for transmitting ultrasonic waves and receiving echo information. A variety of transducer arrays are well known in the art, e.g., linear arrays, convex arrays or phased arrays. The transducer array 214, for example, can include a two dimensional array (as shown) of transducer elements capable of scanning in both elevation and azimuth dimensions for 2D and/or 3D imaging. The transducer array 214 is coupled to a microbeamformer 216 in the ultrasound probe 212. The microbeamformer 216 controls transmission and reception of signals by the transducer elements in the array 214. In this example, the microbeamformer 216 is coupled by the probe cable to a transmit/receive (T/R) switch 218, which switches between transmission and reception and protects the main beamformer 222 from high energy transmit signals. In some embodiments, for example in portable ultrasound systems, the T/R switch 218 and other elements in the system can be included in the ultrasound probe 212 rather than in a separate ultrasound system base. The transmission of ultrasonic beams from the transducer array 214 under control of the microbeamformer 216 is directed by the transmit controller 220 coupled to the T/R switch 218 and the beamformer 222, which receive input from the user's operation of a user interface 224. The user interface 224 may include one or more input devices 250 (e.g., a control panel 252, a touchless interface 254 and/or a touchscreen).

One of the functions controlled by the transmit controller 220 is the direction in which beams are steered. Beams may be steered straight ahead from (orthogonal to) the transducer array 214, or at different angles for a wider field of view. The partially beamformed signals produced by the microbeamformer 216 are coupled to a main beamformer 222 where partially beamformed signals from individual patches of transducer elements are combined into a fully beamformed signal. The beamformed signals are coupled to a signal processor 226. The signal processor 26 can process the received echo signals in various ways, such as bandpass filtering, decimation, I and Q component separation, and harmonic signal separation. The signal processor 226 may also perform additional signal enhancement such as speckle reduction, signal compounding, and noise elimination. The processed signals are coupled to a B-mode processor 228, which can employ amplitude detection for the imaging of structures in the body. The signals produced by the B-mode processor 228 are coupled to a scan converter 230 and a multiplanar reformatter 232. The scan converter 230 arranges the echo signals in the spatial relationship from which they were received in a desired image format. For instance, the scan converter 230 may arrange the echo signal into a two dimensional (2D) sector-shaped format, or a pyramidal or otherwise shaped three dimensional (3D) format. The multiplanar reformatter 232 can convert echoes which are received from points in a common plane in a volumetric region of the body into an ultrasonic image (e.g., a B-mode image) of that plane, as described in U.S. Pat. No. 6,443,896 (Detmer). A volume renderer 234 converts the echo signals of a 3D data set into a projected image of the 3D dataset as viewed from a given reference point, e.g., as described in U.S. Pat. No. 6,530,885 (Entrekin et al.).

In some embodiments, the volume renderer 334 may receive input from the user interface 224. The input may include the given reference point (e.g., viewpoint of a virtual observer), location of a simulated light source, and/or properties of the simulated light source for the rendered projected image. The images from the scan converter 230, multiplanar reformatter 232, and/or volume renderer 234 are coupled to an image processor 236 for further enhancement, buffering and temporary storage for display on an image display 238. The image processor 236 may overlay B-mode images onto the projected images or display the B-mode images concurrently alongside the projected images of the 3D dataset. The volume renderer 234 may render or cause the image processor to render visual cues of various rendering constructs, in some embodiments. In some embodiments, a visual cue of a simulated light source or a cut plane may be rendered in the projected images of the 3D dataset. A graphics processor 240 can generate graphic overlays for display with the images. These graphic overlays can contain, e.g., standard identifying information such as patient name, date and time of the image, imaging parameters, and the like. For these purposes the graphics processor receives input from the user interface 224, such as a typed patient name or other annotations. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. The user interface 242 can also be coupled to the multiplanar reformatter 232 for selection and control of a display of multiple multiplanar reformatted (MPR) images.

FIGS. 3A-3E show output of a volume rendering interface and more specifically images that may be provided by a system in accordance with the present disclosure. FIG. 3A shows a volume rendering 302 (also referred to herein as projection image) of a 3D ultrasound dataset 350 acquired by imaging a fetus 325. A visual cue of a simulated light source 325 is also shown in the rendering 302. The volume rendering 302 is a cut-away view of the imaged volume represented by the 3D ultrasound dataset 350. The cut-away view is obtained by the user interactively cropping the rendered 3D dataset 350 such as by moving a cut plane in and out of the volume until the user has visually identified the desired plane for extracting a B-mode image. The cut-away view is generated by projecting only a portion of the 3D dataset which is coincident with the cut plane and located on one side of the cut plane (e.g., behind the cut plane as perceived from the view point of the virtual observer). The location of the cut plane is coupled to a multiplanar reformatter, which automatically generates the corresponding B-mode 304 image at that plane. In other words, the multiplaner reformatter determines the MPR slice plane based on information provided by the volume renderer responsive to the user's manipulation of the volume. The notion that the MPR automatically generates a B-mode image based on the rendered cut-away view implies that the MPR does not require the user to manually specify the location of the MPR plane, although in some embodiments, the MPR may receive confirmatory user input indicating that the displayed cut-away view corresponds to the desired MPR plane.

Figure 3C:
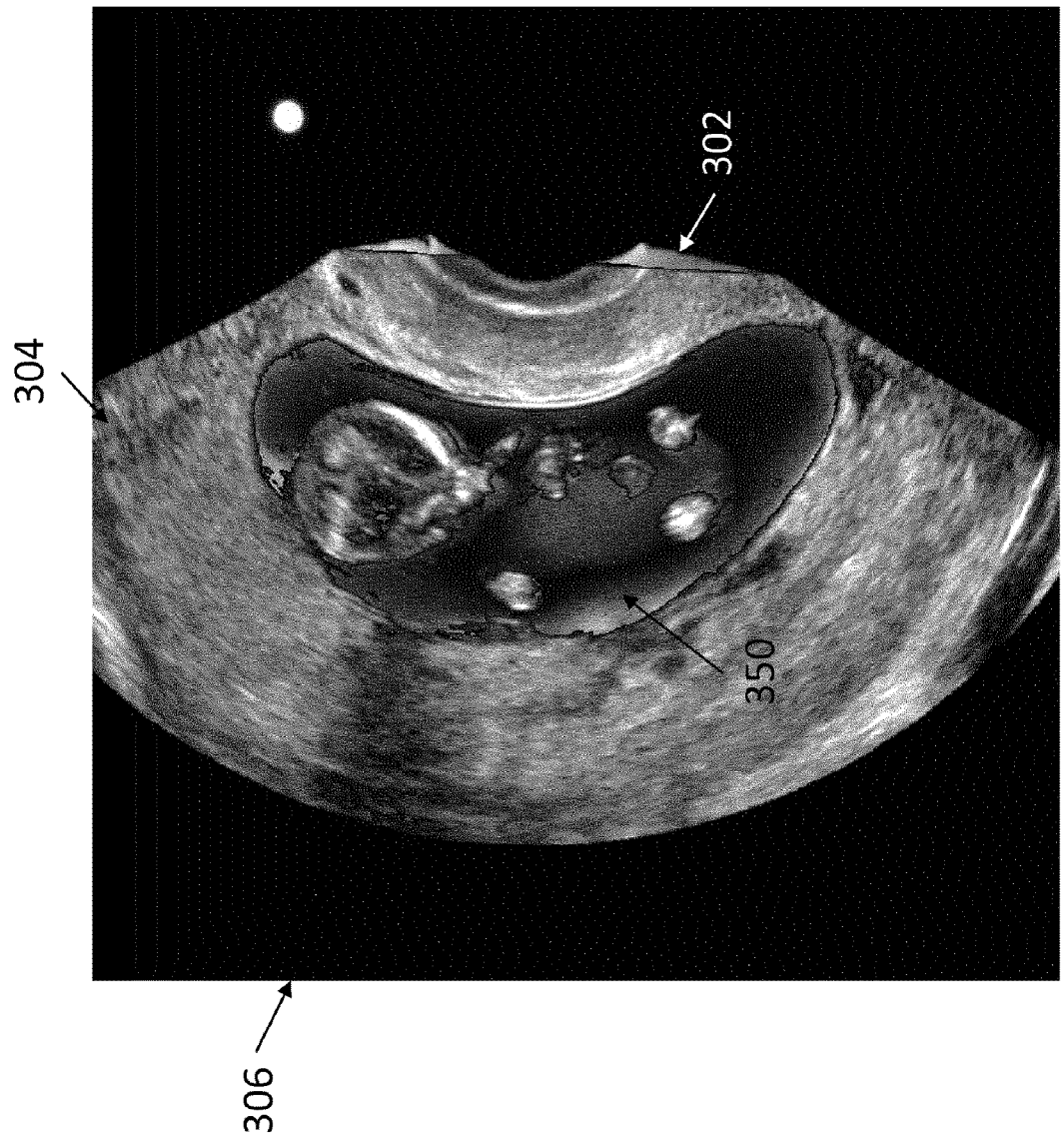

In some examples, the two images (rendering 302 and B-mode image 304) are displayed side by side and each is dynamically updated as the operator crops the volume, or alternatively, the rendering 302 and B-mode image 304 are overlaid in an overlay image 306 shown in FIG. 3C, and the superposed B-mode image is updated in real time to correspond to the cut-away view. In other examples, the B-mode image may not be displayed while the operator crops the volume but is instead output, upon receiving user input confirming that the displayed cut-away view represents the location of the desired cut plane, to memory, for example for inclusion in a report. A volume rendering interface which juxtaposes or superimposes a B-mode image with the rendering of the volumetric data may thus enable the user to intuitively and efficiently select a single or plurality of slices from a volumetric dataset without having to sequentially move through each of the slices that form the volume to identify the desired slice.

In some examples, the rendering of the face of the volume coincident with the cut plane provides a visual cue to the user with regards to the location of the cut plane within the volume, as in the illustrated example. In other examples, an additional visual cue, for example in the form of a planar surface extending beyond the boundary of the rendered volume, may be displayed in the rendering. The user may change the location of the cut plane by selecting and dragging the visual cue. In other examples, changes to the location or orientation of the cut plane may be effected responsive to operation of a given control, such as a track ball or a rotary encoder, when the rendering interface is in volume cropping mode. In embodiments which include a touchless interface, changes to the location or orientation of the cut plane may be effected responsive to movements of a predetermined hand of the user (e.g., the right hand or the left hand). For example, translation of the user's hand in and out of the tracking field of the touchless interface may cause the cut plane to move in and out of the volume, while rotation of the user's hand may cause the cut plane to rotate relative to the volume. In some examples, movement of the cut plane may be limited to only translation along a direction normal to the projection plane.

Figure 3E:
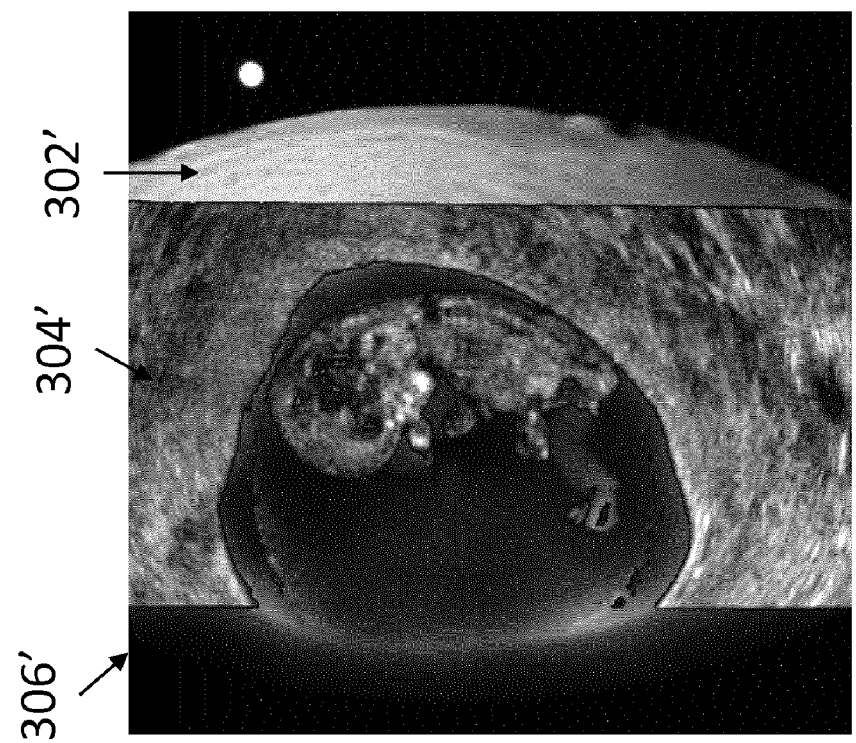
Figure 3D:
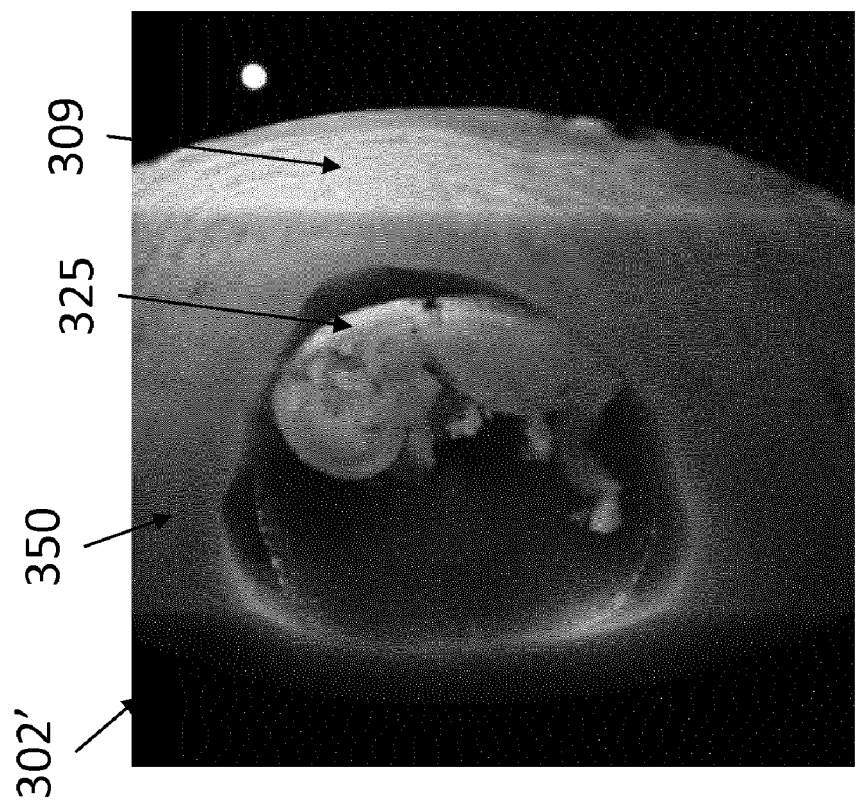

In some examples, the volume may be cropped along multiple directions such as for generating B-mode images of oblique slice planes. In such example, a plurality of cut planes may be activated simultaneously or in sequence. Visual cues of one or more cut planes may be displayed while a cut plane is active (e.g., operable to crop the rendered volume). In some examples, a plurality (e.g., two cut planes) may be active at any given time such that the user can manipulate the location of any of the plurality of cut planes at the same time. In other examples, only a single cut plane (e.g., a cut plane arranged parallel to the projection plane) may be active at any given time and B-mode images may be automatically generated only for planes coincident with the active cut plane. The user may activate another cut plane after deactivating the first cut plane, such as by rotating the volume with respect to the projection plane. For example, the volume rendering 302' in FIG. 3D shows a cut-away view of the 3D dataset 350 cropped using a cut plane which is at an angle to the cut plane used to produce the cut-away view in FIG. 3A. Similar to FIG. 3C, FIG. 3E shows an overlay image 306' of the volume rendering 302' in FIG. 3D with the corresponding B-mode image 304'. As shown in FIGS. 3D and 3E, the 3D dataset 350 may have been cropped in one direction as show by the face 309, following which the relative position of the first cut plane to the volume is maintained while the rendering is updated to show the volume rotated to position the face 309 obliquely to the projection plane. A second cut plane may be activated and manipulated to automatically generate B-mode images at the planes coincident with the second cut plane. In some examples, a second cut plane may default to an orthogonal relationship with a first cut plane such that the operator can easily obtain the standard orthogonal views once one of the three standard views (e.g., coronal, sagittal or axial) has been interactively identified. This may simplify the process of obtaining the standard views especially when the volume rendering and manipulation occurs in real-time and when imaging a moving target such as during fetal or cardiac ultrasound.

Figure 4:
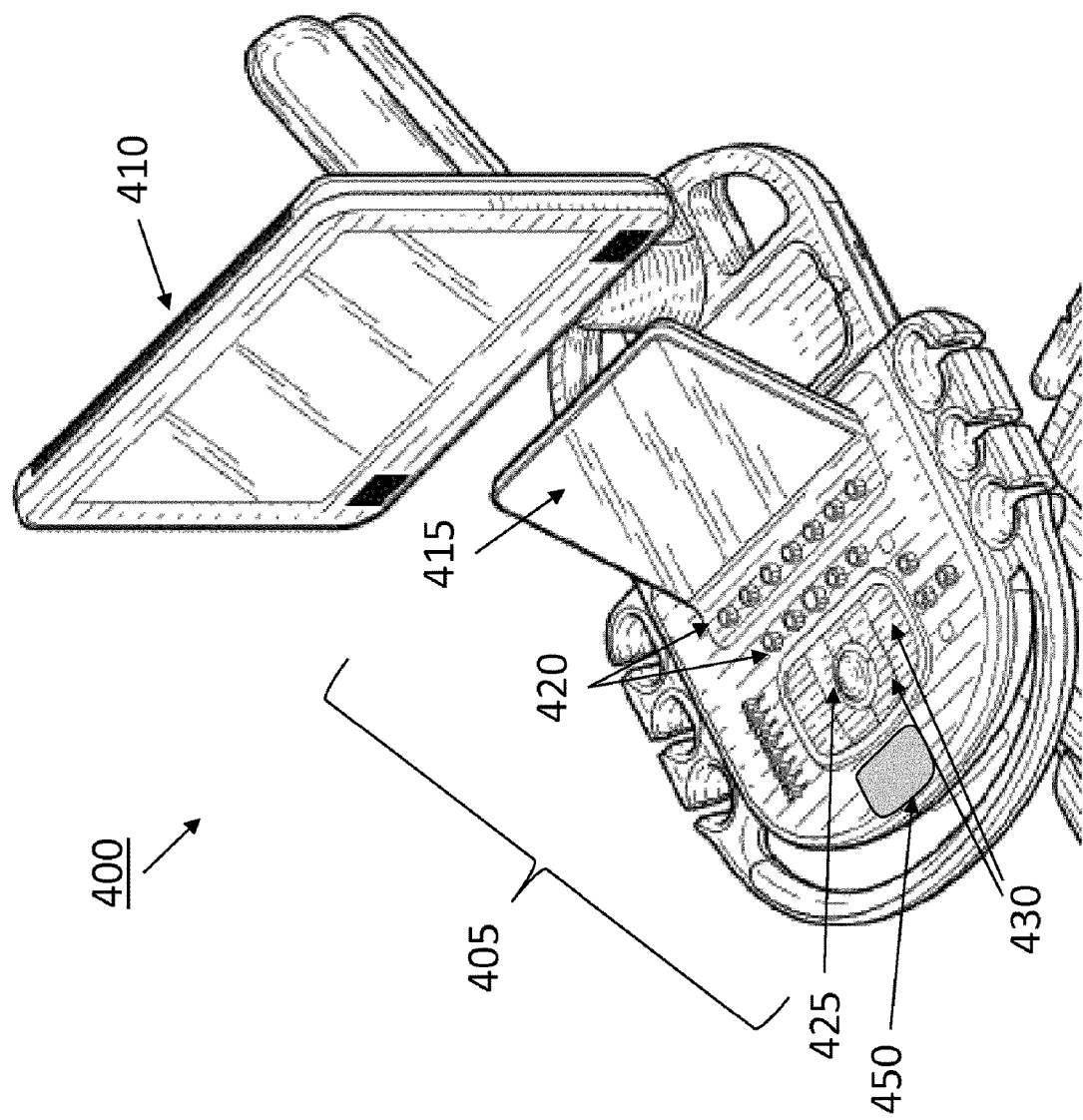
FIG. 4 is an illustration of a portion of an ultrasound imaging system which may embody a volume rendering interface in accordance with the present disclosure.

FIG. 4 shows a portion of an ultrasound system 400 which may embody a volume rendering interface in accordance with the principles of the present invention. The ultrasound system 400 may include some or all of the components of the ultrasound imaging system of FIG. 2. The ultrasound system 400 includes a display 410 and a control panel 405 which includes a variety of physical controls (e.g., a trackball 425 and buttons 430, rotary encoders 420, a touch screen 415, and others). In some examples, the ultrasound system 400 may be operatively coupled to additional displays (not shown). For example, a main display monitor may be provide elsewhere within the examination or operating room, which may provide a more convenient viewing location for the user during data acquisition. User inputs for manipulating a volume rendered on the display 410 and/or display 415 may be received via the control panel 405. In some examples, the ultrasound system 400 may be equipped with a touchless interface, which may include a motion tracking device 450. The motion tracking device 450 may be configured to optically track an object, such as the user's hand(s) when placed in the tracking field of the device 450.

The motion tracking device 550 may be provided on or proximate the control panel 405. In other examples, the motion tracking device 450 may be located elsewhere, such as on or near a patient examination table. The motion tracking device 550 may be part of a touchless interface implemented in accordance with any of the examples in co-pending U.S. Patent Application No. 62/418,313, titled "Systems and methods for three dimensional touchless manipulation of medical images," and published as International Application No. PCT/EP2017/067193, which application is incorporated herein by reference in its entirety for any purpose.

Figure 5:
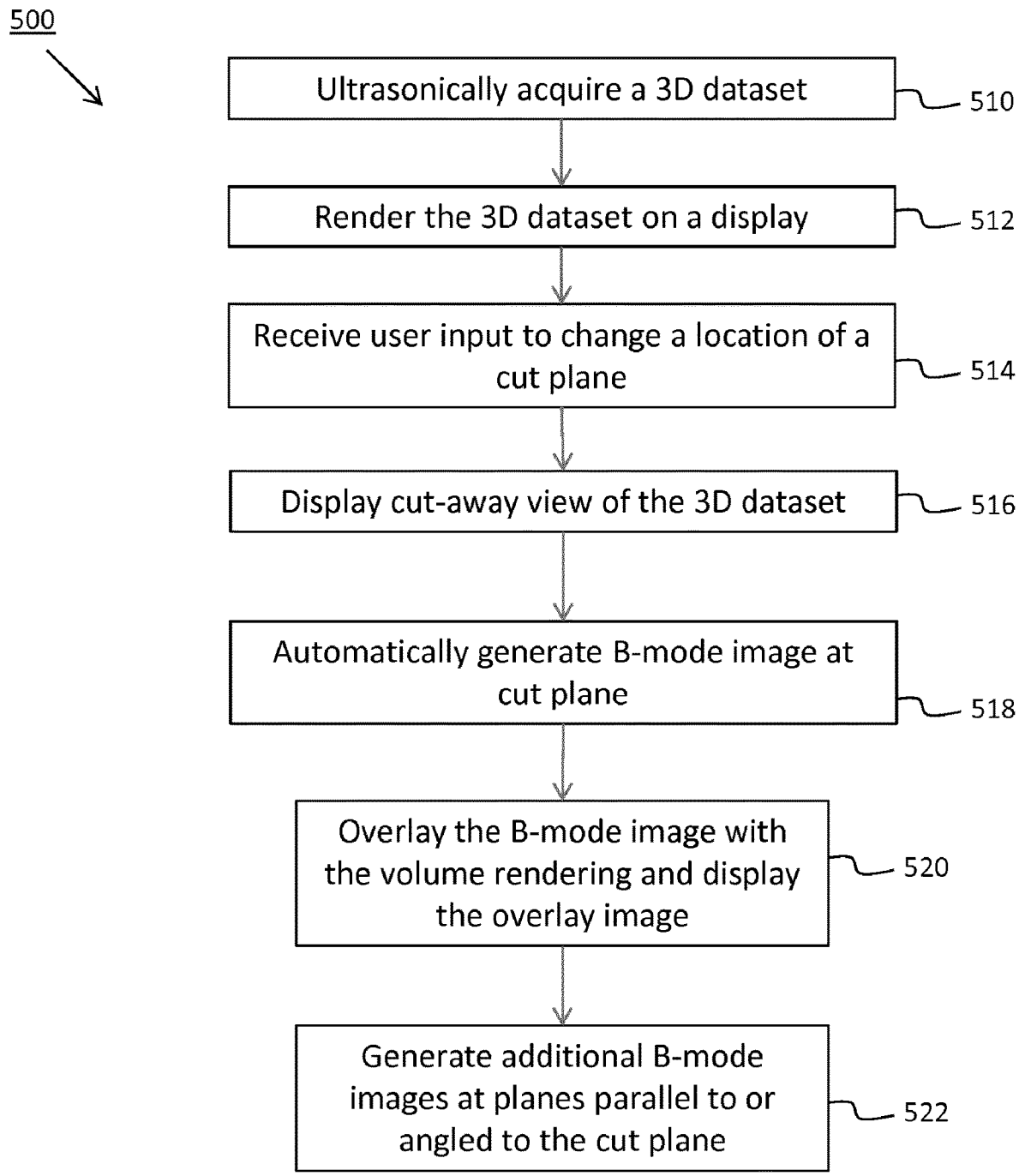
FIG. 5 is a flow diagram
Figure 6:
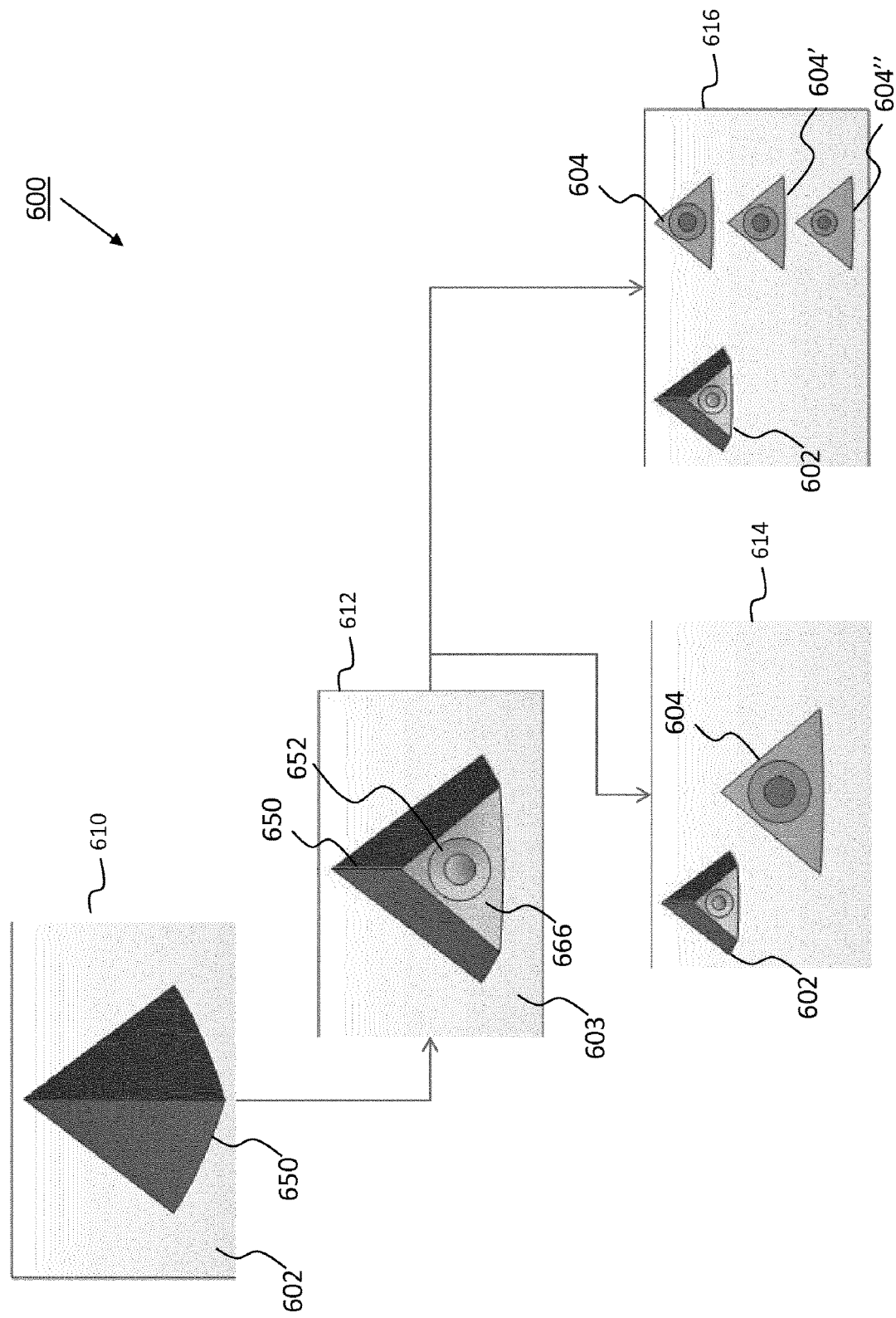
FIG. 6 is a block diagram of steps in a rendering and manipulation process
Figure 7:
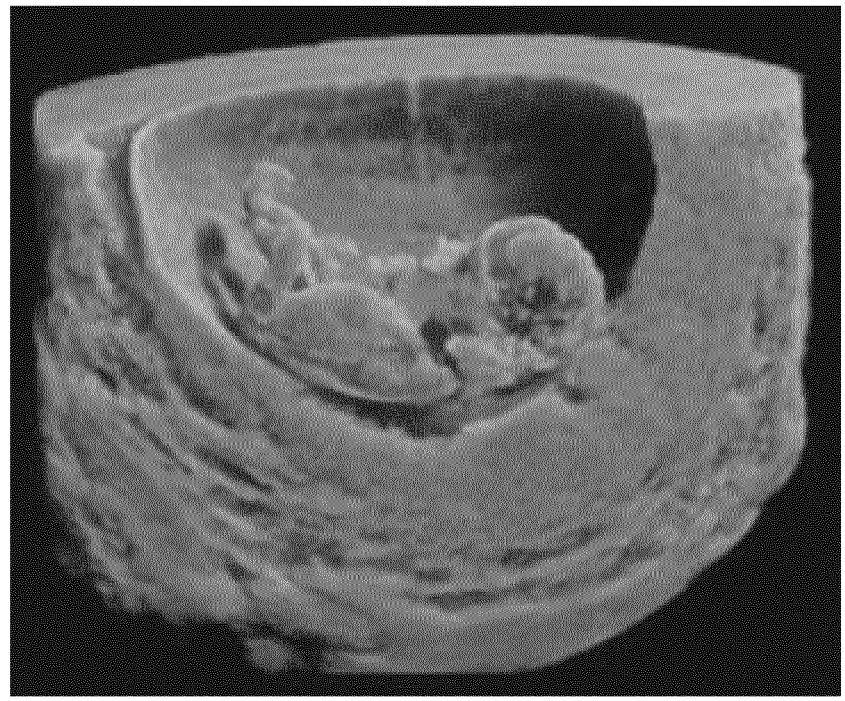
FIG. 7 illustrates an advanced rendering of a ten-week fetus.
Figure 8:
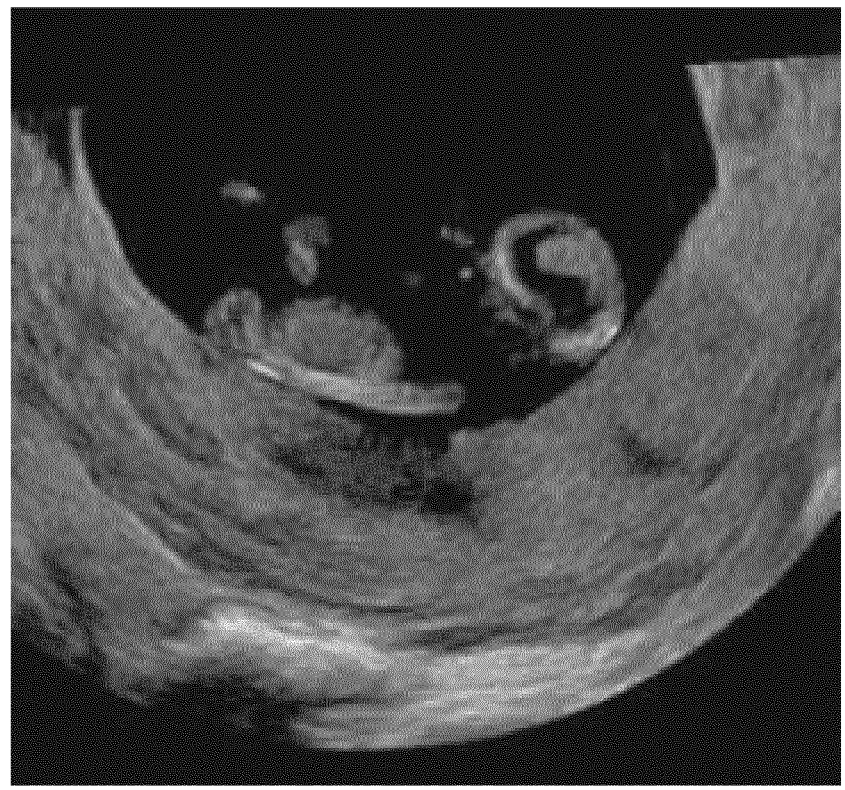
FIG. 8 is a 2D image representing a proximal cut plan of data used to produce the rendered image of FIG. 7.
Figure 9:
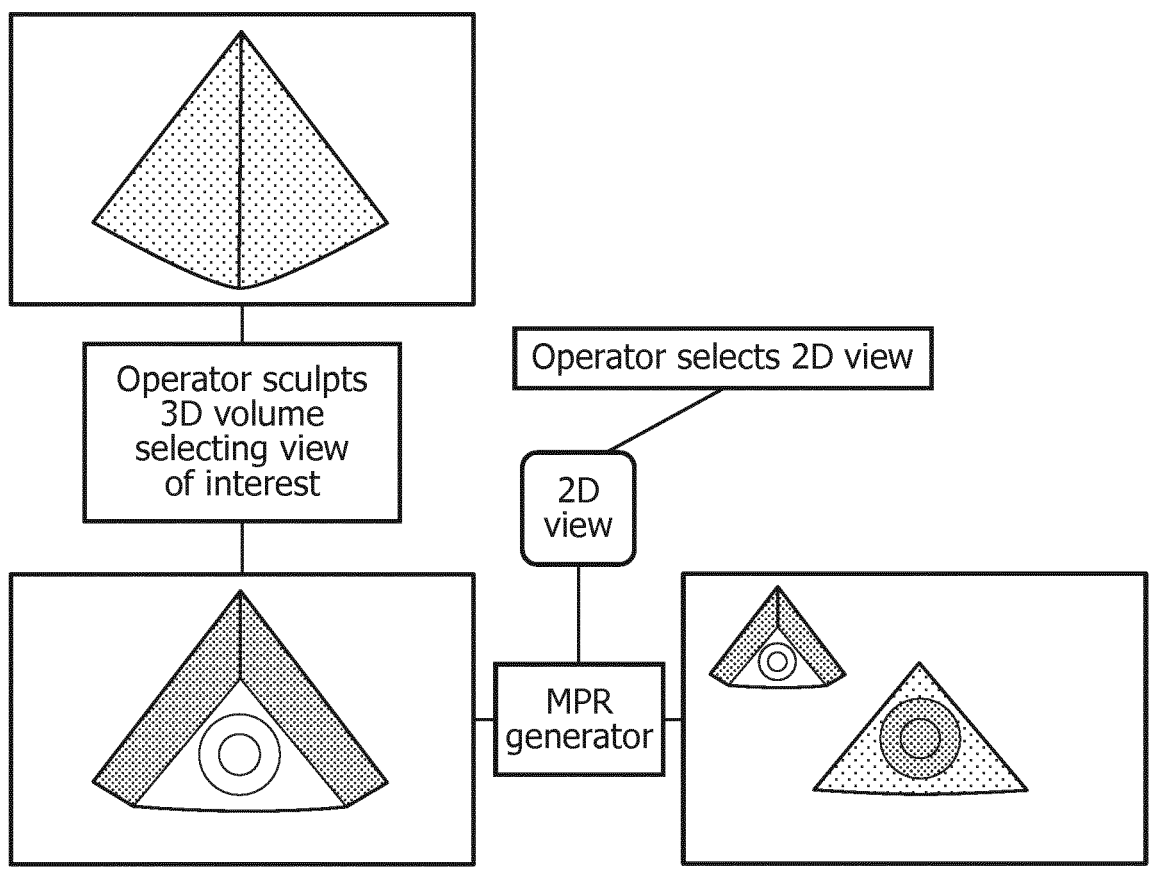
FIG. 9 illustrates a process for a system to generate a proximal slice plane on command.
Figure 10:
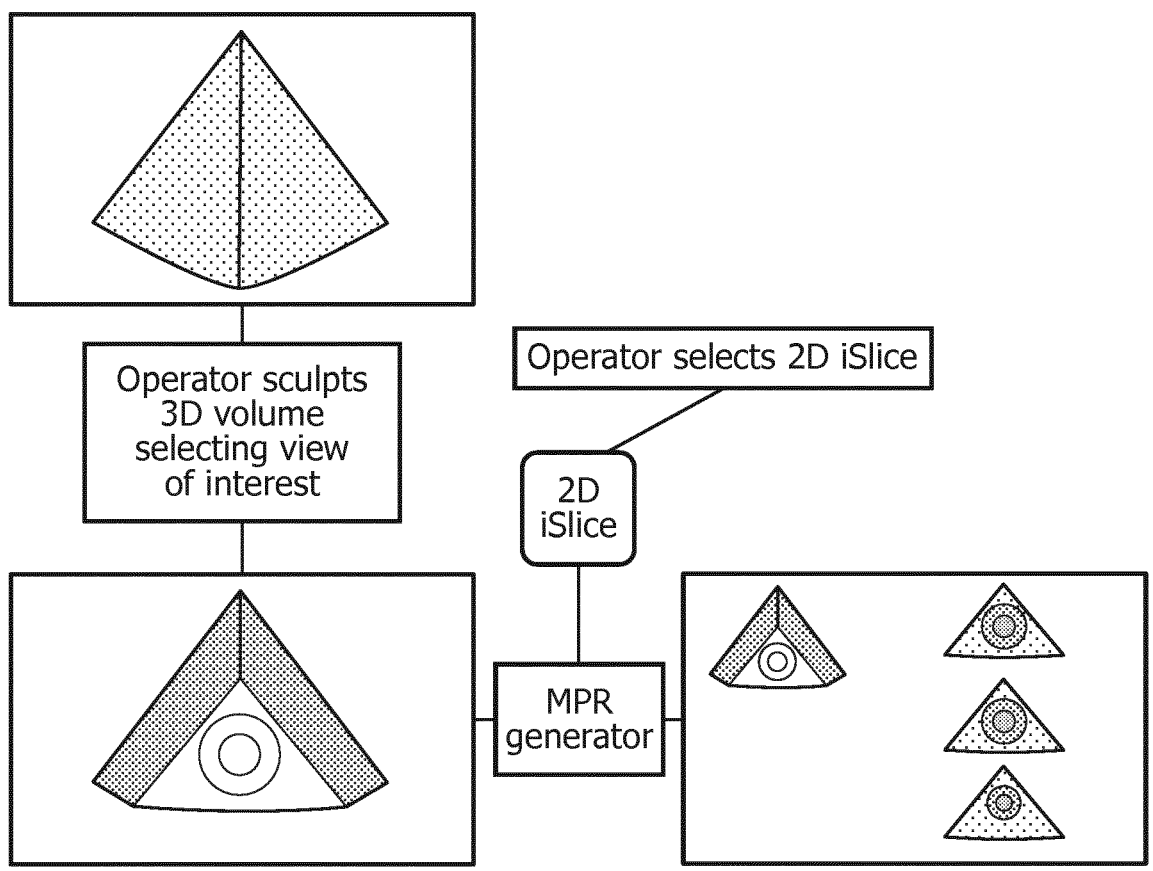
FIG. 10 illustrates a process for a system to generate a proximal slice plane on command as well as one or more planes anterior and distal to said slice plane.
Figure 11:
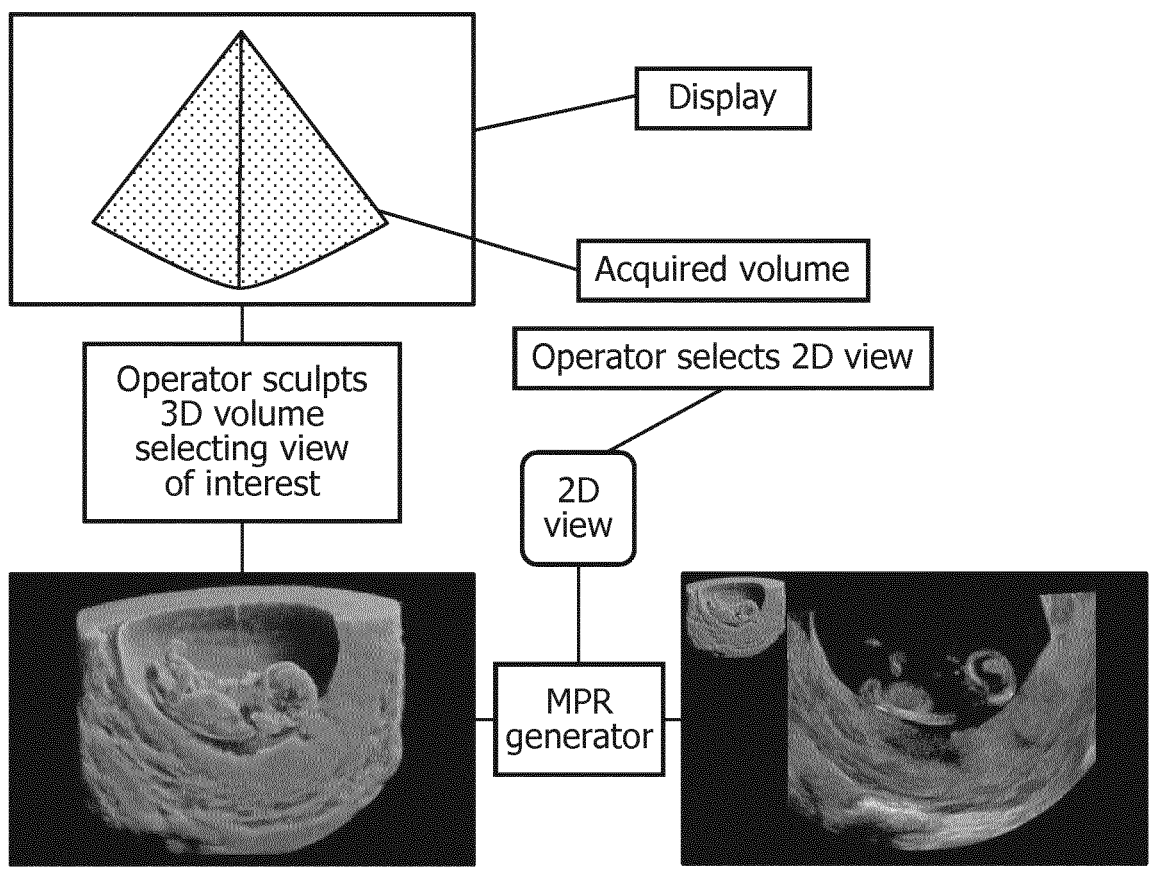
FIG. 11 illustrates an alternative process embodiment to FIG. 9.

Referring to FIGS. 5 and 6, an exemplary technique for generating a B-mode image from 3D ultrasound data will be described. While this example is described with reference to 3D ultrasound data, it will be understood that the principles of the present disclosure may be implemented with 3D datasets obtained using different imaging modalities. FIG. 5 shows a flow diagram of a process 500 for generating a B-mode image from 3D ultrasound data. The process 500 will be described with reference also to the block diagram illustrating aspects of the volume rendering interface 600 in FIG. 6.

The process 500 may be performed by an ultrasound imaging system, such as system 200. The process 500 begins by accessing a 3D dataset 650. In some examples, accessing the 3D dataset 650 may include retrieving the 3D dataset 650 from memory. For example, the 3D dataset 650 may have been acquired by an ultrasound probe, such as ultrasound probe 212 of system 200, at a time prior to rendering images from the 3D dataset 650. In some examples, accessing the 3D dataset 650 may include acquiring the 3D dataset 650, as shown in block 510. One or more of the steps of process 500 may be performed in real time during data acquisition.

The process 500 continues by generating a rendering of the 3D dataset 650, as shown in block 512. For example, as shown in box 610 of FIG. 6, a 2D projection image 602 of the 3D dataset 650 may be generated and displayed on a display (e.g., display 238 of system 200). The display is part of a user interface which is operatively associated with the rendering engine (e.g., volume renderer 112 of system 100 or volume renderer 234 of system 200) and configured to receive inputs to manipulate the 3D dataset 650, including inputs to crop the 3D dataset 650 as shown in box 612.

The process 500 continues by receiving user inputs to change a location of a cut plane in relation to the 3D dataset, as shown in block 514, and displaying a cut-away view of the 3D dataset, as shown in block 516. For example, the user dynamically crops the volume by moving a cut plane 666 in relation to the 3D dataset 650 to produce a cut-away view 603 in which only a portion of the volume coincident with and located on one side of the volume (e.g., behind the cut plane from the viewer's perspective) is rendered on the display. In the cut-away view, the portion of the 3D dataset which is behind the cut plane is rendered (also referred to as displayed portion), while the portion of the 3D dataset which is disposed on the opposite side of the cut plane 666 (i.e. between the cut plane 666 and the projection plane) is not rendered so as to expose the internal anatomical structure of the imaged volume, which may include a region of interest 652. As the operator moves the cut plane 666, the volume rendering is updated in real time to show a dynamically changing cut away view of the 3D dataset 650. The dynamically changing cut-away view enables the operator to visualize anatomical structures internal to the imaged volume and visually identify a relevant plane for generating one or more B-mode images, as shown in boxes 614 and 616. While the volume rendering is updated to show the dynamically changing cut-away view, shading information is calculated for those surfaces which remain visible in the portion of the 3D dataset that is displayed in the cut away view, thereby providing a perception of depth to the user.

The process 500 continues by generating a B-mode image at the location of the cut plane, as shown in block 518. The B-mode image 604 for any cut-away view that is displayed may be automatically generated (e.g., without further input from the user), and in some cases automatically displayed on the display concurrently with the volume rendering, as shown in boxes 614 and 616. In some examples, the B-mode images (e.g., 604, 604', 604") may be displayed adjacent to the volume rendering 602. In other examples, a single B-mode image corresponding to the cut plane may be overlaid on the volume rendering and thus dynamically updated as the cut-away view is updated, e.g., as shown in block 520 of process 500. In some examples, the generation of B-mode images may be automatic once the volume rendering interface receives user input confirming selection of automatic B-mode image generation mode. In yet other examples, while a B-mode image is reconstructed responsive to receiving a location of the cut plane from the volume renderer (i.e., without requiring the user to specify the location of the slice plane), the B-mode image is nonetheless not generated until receipt of confirmatory input from the user to generate the B-mode image, which can be provided by the user pushing a button on the control panel, the probe, tapping a location on a touch screen or inputting a given touchless command. In this regard, the interface allows the user to scroll to the desired cut plane before generating B-mode images, which may reduce the use of computational resources.

In further example, a plurality of B-mode images may be generated, as shown in box 616. For example, additional B-mode images (604', 604") may be generated and displayed, or in some cases, only stored without being displayed for later inspection. The additional B-mode images may be parallel slices spaced at a given distance from the selected cut plane 666. In some examples, oblique slices, in some cases orthogonal slices, may be automatically generated following interactive selection of the cut plane 666. The spacing and/or the angle between slices may be user configurable and may be set prior to entering volume cropping mode or after the desired cut plane has been visually identified. In further examples, the volume rendering interface may enable the user to specify the direction of parallel spaced slices (e.g., behind or forward in relation to the selected cut plane). The volume rendering interface may be further configured to enable the user to specify which, if any, of the B-mode images should be automatically included in a report. In this manner, the volume rendering interface and techniques described may provide a more intuitive and/or interactive approach to generating 2D slice images (e.g., B-mode images) through an imaged volume as may have been previously possible.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
   an ultrasound probe configured to receive ultrasound echoes from a subject to image a volume of the subject;
   a scan converter configured to arrange echo signals in a 3D dataset corresponding to the imaged volume;
   a volume renderer configured to generate, from the 3D dataset, a volume rendering of the imaged volume and receive user input indicative of a location of a cut plane through the imaged volume for generating a cut-away view of the volume rendering, the cut-away view comprising a two dimensional (2D) projection image of the 3D dataset, in which a portion of the 3D dataset on one side of the cut plane is included in the 2D projection image while a second portion of the 3D dataset on an opposite side of the cut plane is not included in the 2D projection image;
   a multiplanar reformatter configured to generate, from the 3D datasets, a 2D B-mode image of a slice through the imaged volume at the cut plane, wherein the 2D B-mode image is a different type of image from the 2D projection image of the cut-away view; and
   a user interface comprising:
      a display configured to display the 2D projection image of the cut-away view of concurrently with the 2D B-mode image of the slice, overlaid onto, or displayed next to, the 2D projection image of the cut-away view; and
      an input device configured to enable the user to scroll or drag the location of the cut plane on the display along a first direction through the imaged volume, and wherein the volume renderer and multiplanar reformatter are further configured to dynamically and automatically update, responsive to the scrolling or dragging the cut lane the 2D projection image of the cut-away view and the 2D B-mode image of the slice to each new location of the cut plane.

2. The ultrasound imaging system of claim 1, wherein the input device comprises a trackball, a touchpad, or a touch screen, and wherein the volume renderer and multiplanar reformatter are configured to dynamically automatically update the 2D projection image of the cut-away view responsive to scrolling or dragging the cut plane via the trackball, touchpad, or touch screen.

3. The ultrasound imaging system of claim 1, wherein the input device comprises a hand-tracking device configured to track a movement of a user's hand when the user's hand is presented in a tracking field of the hand-tracking device, and wherein the volume renderer is configured to translate the movement of the user's hand to movement of the cut plane for dragging the cut plane through the imaged volume displayed on the display.

4. The ultrasound imaging system of claim 3, wherein the hand-tracking device is configured to track both of the user's hands when presented in the tracking field, and wherein the volume renderer is configured to translate the movement of one of the user's hands to movement of the imaged volume relative to a projection plane and to translate the movement of the other one of the user's hands to movement of the cut plane relative to the imaged volume.

5. The ultrasound imaging system of claim 3, wherein the cut plane is a first cut plane, wherein the hand-tracking device is configured to track both of the user's hands when presented in the tracking field, and wherein the volume renderer is configured to translate the movement of one of the user's hands to movement of the first cut plane relative to the imaged volume, and to translate the movement of the other one of the user's hands to movement of a second cut plane relative to the imaged volume.

6. The ultrasound imaging system of claim 1, wherein the input device comprises a hand-tracking device configured to track a movement of a user's hand or a portion thereof when presented in a tracking field of the hand-tracking device, wherein the hand-tracking device is configured to generate tracking data responsive to the movement, and wherein the volume renderer is configured to update the 2D projection image based on the tracking data.

7. The ultrasound imaging system of claim 1, wherein the multiplanar reformatter is further configured to generate at least one of a plurality of B-mode images at parallel slice planes spaced apart from the location of the cut plane or one or more additional B-mode images at slice planes oblique to the cut plane.

8. The ultrasound imaging system of claim 7, wherein the input device is configured to provide a user interface element operable to receive user input for specifying a spacing of the parallel slice planes, an angle between the oblique planes, or both.

9. The ultrasound imaging system of claim 1, wherein the multiplanar reformatter is configured to automatically generate the B-mode image responsive to receiving an indication of the location of the cut plane.

10. A method comprising:
receiving a 3D dataset corresponding to an ultrasonically imaged volume of biological tissue;
generating a volume rendering of the 3D dataset;
displaying the volume rendering on a display, wherein the volume rendering displays the 3D dataset fully or as a cut-away view comprising a two dimensional (2D) projection image of the 3D dataset, in which a portion of the 3D dataset on one side of a cut plane is included in the 2D projection image while a second portion of the 3D dataset on an opposite side of the cut plane is not included in the 2D projection image;
receiving user input for dynamically changing, by scrolling or dragging the cut plane on the display, a location of the cut plane relative to the 3D dataset;
automatically generating, from the 3D dataset, a B-mode image of a slice through the 3D dataset at a plane coincident with the cut plane and displaying the B-mode image as an overlay on, or next to, the cut-away view;
dynamically and automatically updating, while scrolling or dragging the cut plane on the display, the cut-away view and the corresponding B-mode image to reflect the dynamically changing location of the cut plane.

11. The method of claim 10, wherein the scrolling or dragging of the cut plane is responsive to user input from a trackball, a touchpad, or a touch screen.

12. The method of claim 10, further comprising receiving input to move the 3D dataset relative to a projection plane while maintaining a relative position between the cut plane and the 3D dataset.

13. The method of claim 10, wherein the cut plane is a first cut plane, the method further comprising receiving input to change a location of a second cut plane relative to the 3D dataset.

14. The method of claim 10, wherein the scrolling or dragging of the cut plane is responsive to user input received via a touchless interface.

15. The method of claim 10, wherein the scrolling or dragging of the cut plane comprises tracking a first movement of one of the user's hands and translating the first movement to movement of the cut plane relative to the imaged volume, the method further comprising tracking a second movement of the other one of the user's hands and translating the second movement to a change is a position of the 3D dataset relative to a projection plane.

* * * * *